(12) United States Patent
Sawada

(10) Patent No.: US 6,574,303 B2
(45) Date of Patent: Jun. 3, 2003

(54) RADIATION INSPECTION APPARATUS AND RADIATION INSPECTION METHOD

(75) Inventor: Ryoichi Sawada, Joyo (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 10/123,675

(22) Filed: Apr. 16, 2002

(65) Prior Publication Data

US 2002/0168047 A1 Nov. 14, 2002

(30) Foreign Application Priority Data

Apr. 17, 2001 (JP) .................................. 2001-118628

(51) Int. Cl.[7] .............................................. G01N 23/04
(52) U.S. Cl. ...................................... 378/58; 250/359.1
(58) Field of Search ........................... 378/58, 23, 24, 378/25, 54, 56, 57; 250/358.1, 359.1, 360.1; 348/200; 382/143, 141

(56) References Cited

U.S. PATENT DOCUMENTS

RE35,423 E  *  1/1997  Adams et al. ................. 378/58
6,023,497 A  *  2/2000  Takahashi et al. ............ 378/57

* cited by examiner

Primary Examiner—Drew A. Dunn
Assistant Examiner—Irakli Kiknadze
(74) Attorney, Agent, or Firm—Rankin, Hill, Porter & Clark LLP

(57) ABSTRACT

A radiation inspection apparatus calculates the difference between pixel data of each pixel, which is outputted from radiation detector 3, and pixel data of each of surrounding pixels thereof. Then, the apparatus obtains a total of circumference length of an object to be inspected WA by totalizing the number of pixels, the gray level data obtained by difference processing correspondingly to each of which is within a predetermined gray level range of gray level profile from XL to XH. Thus, the apparatus determines from the value of the total of the circumference length of the object whether or not a crack or a nick occurs in the object.

5 Claims, 4 Drawing Sheets

WA

RADIATION INSPECTION APPARATUS AND RADIATION INSPECTION METHOD

BACKGROUND OF THE INVENTION

1. Field of the Invention

The present invention relates to a non-destructive inspection apparatus or method for inspecting drugs and food-products. More particularly, the present invention relates to a radiation inspection apparatus and a radiation inspection method suitable for inspecting an occurrence of a crack or a nick of a packaged object, whose inside cannot be observed with visual light owing to packaging materials.

2. Description of the Related Art

Hitherto, an inspection apparatus using visual or infrared light has been known as an apparatus for inspecting an occurrence of a crack and a nick of a packaged food-product. This inspection apparatus using visual light or infrared light usually irradiates an object to be inspected, which is packaged, with visual or infrared light and then receives light reflected or transmitted by the object by using a CCD camera. Thus, the inspection apparatus obtains image information concerning the inside of a package and determines whether or not abnormality, such as a crack and a nick, of the object included in the package occurs according to the shape thereof.

Meanwhile, in recent years, many kinds of aluminum foil and boxes, which are disabled to transmit light, have been employed as the manners of packaging food-products and drugs. Such inspection apparatuses using light are no use to inspect an occurrence of a crack or nick of the object packaged in such a manner.

Moreover, the inspection apparatus using light has a problem that, even if a packaging material constituted by a light-transmissive material is used, a result of inspection is significantly affected by the coloring of the surface of the packaging material.

It is sufficient for seeing the inner situation of the package wrapped by the packaging material made of a non-transmissive material therethrough to use an inspection apparatus using radiation, such as X-rays. In a conventional radiation inspection apparatus, radiation transmitted through the object to be inspected is detected by a one-dimensional or two-dimensional radiation detector. Then, a pattern of a perspective two-dimensional image of the object contained in the package is recognized by performing image processing using pixel information. Thus, the conventional apparatus determines whether or not abnormality, such as a crack, occurs in the object included in the package occurs. Therefore, the conventional apparatus has problems that large-scale image processing should be performed so as to realize a high-speed inline system, and that both the hardware and software of the apparatus are too costly.

SUMMARY OF THE INVENTION

The invention is accomplished in view of such circumstances. Accordingly, an object of the invention is to provide a radiation inspection apparatus and a radiation inspection method that does not need large-scale image processing, which is needed by the conventional apparatus, that the hardware and software for image processing are relatively simple, and that it can reliably be determined with a low-cost configuration whether or not a crack or a nick occurs in an object packaged by a non-transmissive material.

To achieve the foregoing object, according to the invention, there is provided a radiation inspection apparatus, which comprises a radiation generator for generating radiation toward an object to be inspected; a radiation detector disposed in such a way to face the radiation generator, for detecting the radiation transmitted through the object to be inspected and outputting a pixel data of each pixel consisting an image of the object to be inspected; and a data processor unit for performing data processing by using the pixel data outputted from the radiation detector. In this apparatus, the data processor unit calculates a difference between that pixel data of each pixel, which is outputted from the radiation detector, and the pixel data of each of surrounding pixels thereof, and obtains a total of a circumference length of the object to be inspected by totalizing the number of pixels, gray level data obtained by difference processing correspondingly to each of which is within a predetermined gray level range, and determines from a total of the circumference length of the object whether or not a crack or a nick occurs in the object.

The invention obtains an image, in which the pixel gray level of a part corresponding to the contour portion of the object differs from those of the remaining parts thereof, by obtaining the difference between the pixel data of each pixel consisting an image of the object and that of each of the surrounding pixels thereof. The invention achieves the desired purpose by totalizing the number of pixels, whose pixel gray levels are within a predetermined gray level range, and by then determining from a total number of such pixels whether or not a crack or a nick occurs in the object on the basis of the fact that the pixel gray level of the part corresponding to the contour portion differs from those of the remaining parts thereof, instead of recognizing a pattern from image information corresponding to the contour portion.

That is, the difference between the pixel data of each pixel consisting a radiation perspective image of an object to be inspected and each of the surrounding pixels thereof is calculated, so that each of parts corresponding to the contour portions of the object to be inspected has a pixel gray level, which differs from the gray level of parts corresponding to the other portions thereof, and which usually has a deeper (or darker) value than the value of the gray level of parts corresponding to the other portions. Thus, a gray level range, which would include the gray levels of pixels of the part corresponding to the contour portion, is preliminarily set. After the calculation of the difference, a total number of pixels, whose gray levels are within the predetermined gray level range, is calculated. Thus, a total of circumference length of the object to be inspected is obtained. In the case that a crack or a nick occurs in the object, the total of circumference length of the object is longer than that in the case that neither cracks nor nicks occur in the object. Consequently, it can be determined more reliably and easily whether or not cracks and nicks occur therein. Further, software for performing such data processing is simple, as compared with software for pattern recognition by performing image processing on a radiation perspective image. Thus, such data processing can be performed at a high speed by using relatively-low-capacity low-speed hardware.

DETAILED DESCRIPTION OF THE INVENTION

Hereinafter, an embodiment of the invention is described with reference to the accompanying drawings.

Figure 1:
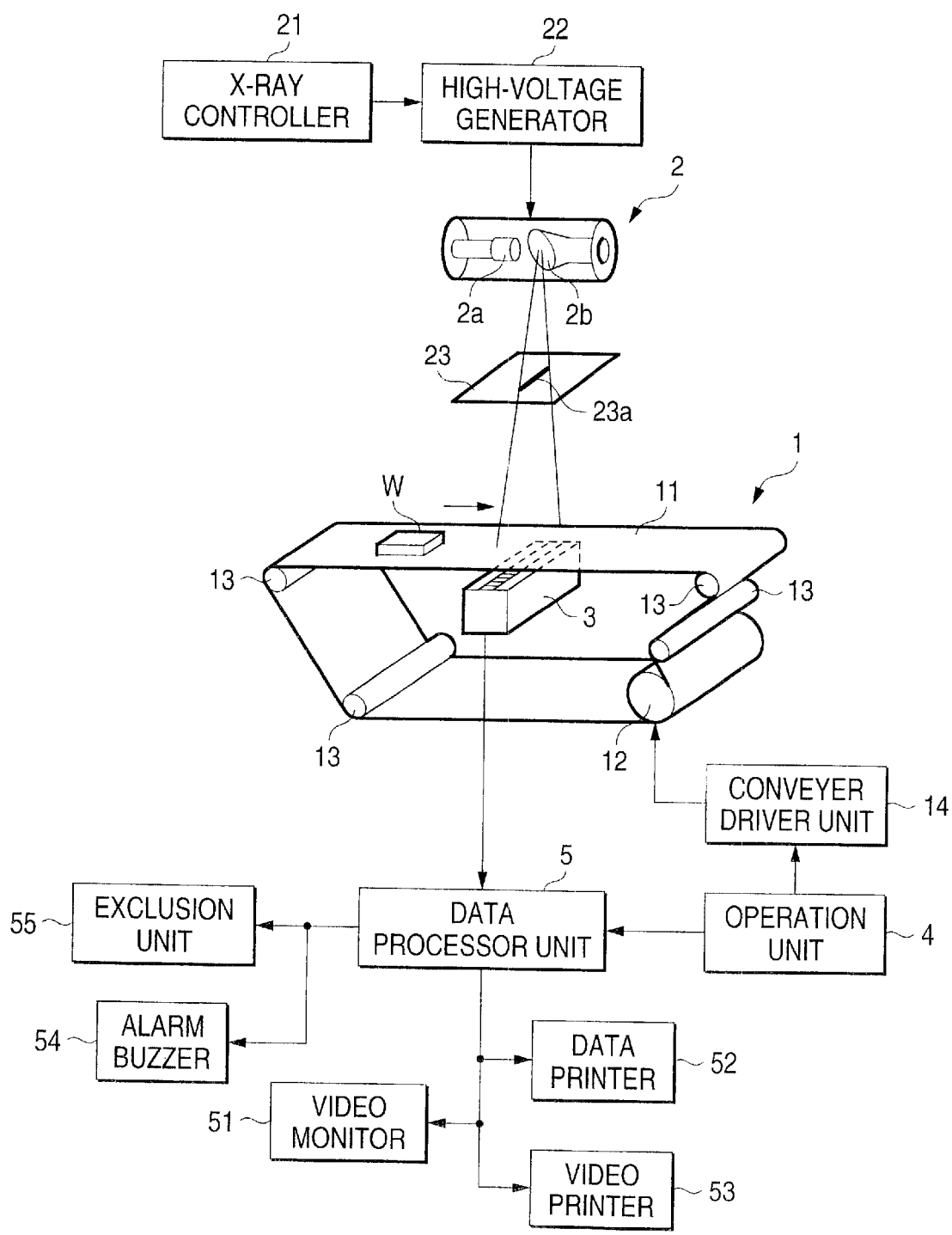
FIG. 1 is a view illustrating the configuration of a radiation inspection apparatus according to an embodiment of the invention.

FIG. 1 is a view illustrating the configuration of a radiation inspection apparatus according to an embodiment of the invention and describing both of a schematic diagram, which shows a mechanical configuration of a primary part of the embodiment, and a block diagram that shows a system control line of the primary part of the embodiment.

An object to be inspected W is put on a loop belt 11 of a conveyer system 1 and conveyed at a constant speed. Above the conveyer system 1, an X-ray tube 2 is disposed in a position in which an X-ray optical axis thereof is directed perpendicularly and downwardly. Moreover, a one-dimensional X-ray detector 3 is disposed perpendicularly under the X-ray tube 2 in such a way as to face the X-ray tube 2 in a state in which the loop belt 11 of the conveyer system 1 is interposed between the X-ray tube 2 and the one-dimensional X-ray detector 3.

The conveyer system 1 includes the loop belt 11, and a drive roller 12 and a plurality of driven rollers 13, over which the belt 11 is looped. A motor (not shown), which is adapted to rotate and drive in response to a, drive signal supplied from a conveyer driver unit 14 by operating a switch provided on an operation unit 4, provides rotation to the drive roller 12. Rotation of this drive roller 12 causes the loop belt 11 to move under the guide of each of the rollers and to convey the object to be inspected W at a constant speed in a direction of an arrow in this figure.

A high-voltage generator 22 controlled by an X-ray controller 21 applies a high voltage to between an anode 2a and a cathode 2b of the X-ray tube 2, so that the X-ray tube 2 produces X-rays. A lead slit member 23 is provided between the X-ray tube 2 and the conveyer system 1. The lead slit member 23 has a slit 23a formed therein in such a way as to extend in a direction perpendicular to a conveying direction, in which the conveyer system 1 conveys the object to be inspected W. X-rays outputted from the X-ray tube 2 pass through the slit 23a thereby to produce X-ray fan beams each diverging in the direction of width of the conveyer system 1.

The one-dimensional X-ray detector 3 comprises a scintillator, and a MOS image sensor on which a plurality of devices are arranged like a line. Incident X-rays are converted by the scintillator into visual light, which is detected by each of the devices of the MOS image sensor in every very short constant time intervals. Each of the devices outputs a detection signal, whose level corresponds to an amount of incident X-ray radiation, every moment.

The detection signal outputted from each of the devices of the one-dimensional X-ray detector 3 is taken in by a data processor unit 5. The data processor unit 5 displays an X-ray perspective image, whose pixel gray level information is represented by the detection signal from each of the devices, on the screen of a monitor 51. Further, the data processor unit 5 determines, by performing a routine (to be described later) using data, which is outputted from each of the devices of the one-dimensional X-ray detector 3 every moment, whether or not a crack or a nick occurs in the object to be inspected. Furthermore, according to a result of the determination, when it is determined that a crack or a nick occurs, data indicating such a decision is generated. Moreover, as will be described later, an alarm buzzer 54 is sounded. Alternatively, an exclusion unit 55 is driven. Furthermore, data representing such a decision is outputted to a data printer 52, and data representing such an image is outputted to a video printer 53.

Figure 2A:
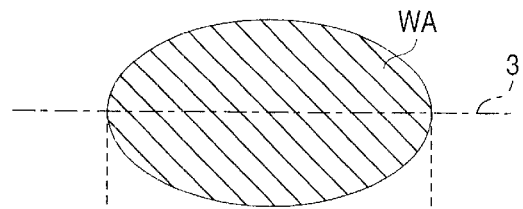
FIG. 2A is a diagram illustrating an X-ray perspective image of an object to be inspected W, which is obtained by using pixel data outputted from a one-dimensional X-ray detector 3.
Figure 2B:
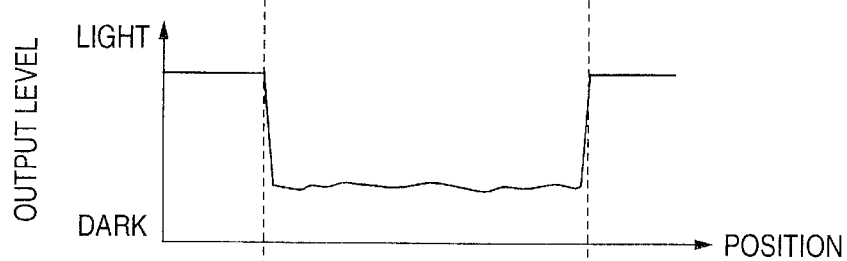
FIG. 2B is a graph illustrating the gray level of each pixel (or channel) outputted from the one-dimensional X-ray detector 3 that is in a state in which the one-dimensional X-ray detector 3 is placed at a predetermined position.
Figure 2C:
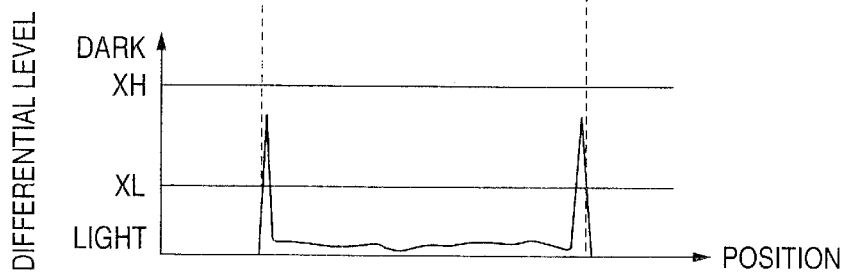
FIG. 2C is a graph illustrating the gray level of each of the pixels, which are in the state illustrated in FIG. 2B after the difference processing.
Figure 2D:
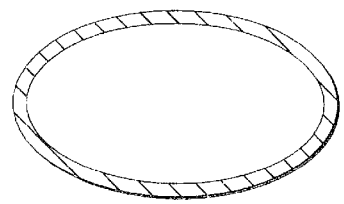
FIG. 2D is a diagram illustrating an image represented by pixel data, which is obtained by the difference processing.

Next, before describing an operation of determining by the data processor unit 5 whether or not a crack or a nick occurs, a difference processing for calculating the difference between pixel data is described herein below. The difference processing itself is a known technique. The data processor unit 5 calculates the difference between the gray level data of each pixel consisting an image and that of each of the surrounding pixels thereof. When an X-ray perspective image of the object to be inspected W obtained from the pixel data outputted from the one-dimensional X-ray detector 3 indicates that one object to be inspected WA is contained in a package, as illustrated in FIG. 2A, the gray level data for each pixel (or channel) is as indicated in FIG. 2B, in a state in which the one-dimensional X-ray detector 3 is disposed at the position indicated in FIG. 2A. Furthermore, when the difference between the gray level data of each pair of the adjacent pixels of every pixel (or channel) is obtained while the one-dimensional X-ray detector 3 is placed at the same position, only the gray levels of pixels of a boundary portion (or contour portion) of the object to be inspected WA are high (that is, only such pixels are dark), as illustrated in FIG. 2C. When an image is constituted by such pixel data after the difference processing, the image is obtained in such a way as to indicate that only the contour portion of the object to be inspected WA is dark, as illustrated in FIG. 2D. The gray level range of gray level profile from XL to XH (to be described later) is set to be a range in which the gray levels of the pixels of the contour portion of the object to be inspected WA shown in FIG. 2D are included, among the pixel data that are obtained after difference processing, as illustrated in FIG. 2C.

Figure 3:
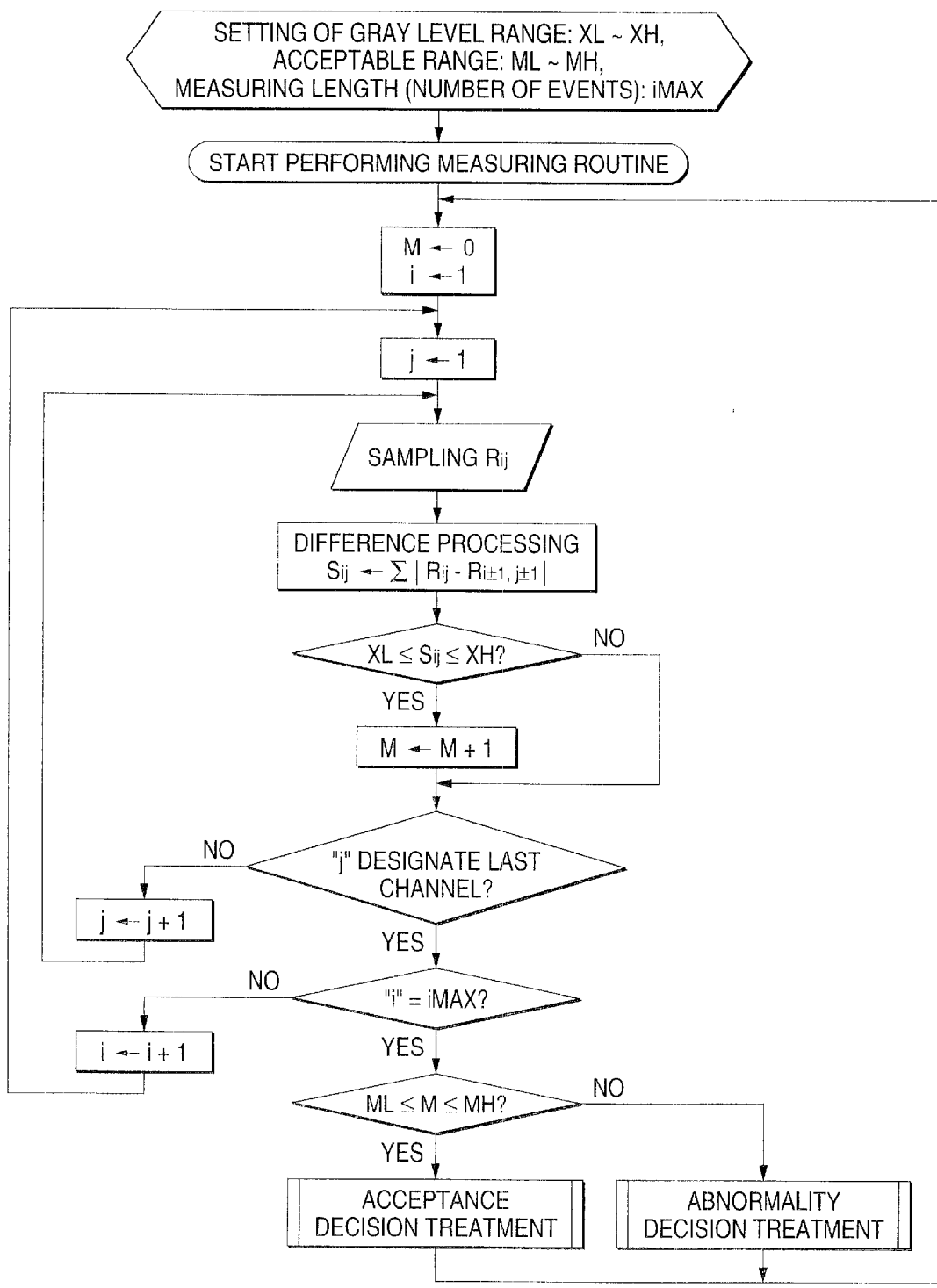
FIG. 3 is a flow chart illustrating a process for determining whether or not a crack or a nick occurs in the object, which is performed by a data processor unit 5 according to the embodiment of the invention.

FIG. 3 is a flow chart illustrating a process for determining whether or not a crack or a nick occurs in the object, which is performed by the data processor unit 5. Hereinafter, an operation of determining in the embodiment of the invention whether or not a crack or a nick occurs is described by referring to this FIG. 3. In this example, it is assumed that the data processor unit 5 determines whether or not a crack or a nick occurs in the single object to be inspected WA accommodated in the package, as shown in FIG. 2A illustrating an X-ray perspective image in a normal state.

In this flowchart, "i" designates an order of outputs of signals from the one-dimensional radiation detector 3 (that is, events), which are caused at very short constant time intervals, in other words, denotes time, and "j" designates No. of each of the devices (or channels) of the one-dimensional radiation detector 3. Therefore, each of pixels of an X-ray perspective image of the object to be inspected W is represented by $R_{ij}$.

Meanwhile, before an automatic operation is performed, the lower limit XL and the upper limit XH of the gray level range of gray level profile of the pixels to be counted are set by operating the ten key provided in the operation unit 4 (see FIG. 2C). Further, the lower limit ML and the upper limit MH of the acceptance range for determining whether or not a crack or a nick of the object occurs are set according to a result of counting the pixels having gray levels included in this gray level range.

Furthermore, the measuring length iMAX is set. This measuring length iMAX designates the number of detection signals outputted from the one-dimensional X-ray detector 3 correspondingly to the single object to be inspected W and taken in by the data processor unit 5. That is, the data processor unit 5 starts to take in outputs of the one-dimensional X-ray detector 3 in response to the generation of an external trigger signal outputted from a commodity detection sensor (not shown) when the leading end of the object to be inspected W having been conveyed on the conveyer system 1 reaches immediately in front of an X-ray irradiating position (i=1). When the number of the taken-in external trigger signals reaches the value of the measuring length IMAX, the data processor unit 5 finishes taking in the outputs of the one-dimensional X-ray detector 3.

Then, initiation of an automatic operation is commanded. Subsequently, the object to be inspected W is supplied onto the conveyer system 1. When the conveyer system 1 starts conveying the object W, initialization is performed in response to an output of the commodity detection sensor so that variables i, j, and M are set as follows i=1, j=1, and M=0. Here, M is a counter incremented by 1 when the gray level data after the difference processing is included in the set gray level range of gray level profile from XL to XH. Then, the data processor unit 5 takes in pixel information of each of pixels $R_{1j}$ in the case of the first event (that is, in the case that i=1). Subsequently, the data processor unit 5 calculates the difference between the gray level data of each pixel and that of each of the surrounding pixels thereof, on the pixels respectively, which are taken in at i=1 and correspond to j of the devices of the one-dimensional X-ray detector 3, correspondingly to "j" whose value changes from 1 to No. of the last channel. Then, it is determined whether or not each of difference values $S_{ij}$ is included in the gray level range of gray level profile from XL to XH. In the case that each of the difference values $Si_{ij}$ is included in the gray level range of gray level profile from XL to XH, M is incremented by 1.

Upon completion of determining correspondingly to each of all the channels whether or not the differential value is included in the gray level range, the data processor unit 5 next takes in pixel information of each of pixels $R_{2j}$ in the case of the second event (that is, in the case that i=2). The data processor unit 5 calculates difference values $S_{ij}$ respectively corresponding to all the channels, similarly as the case that i=1. Then, at each occurrence of the difference value included in the gray level range, M is incremented by 1. When the variable "i" reaches iMAX, it is decided whether or not the value M is included in the predetermined acceptance range of values ranging from ML to MH. Thus, it can correctly be known from this determination whether or not a crack or a nick occurs in the object to be inspected WA contained in the package WB.

Figure 4A:
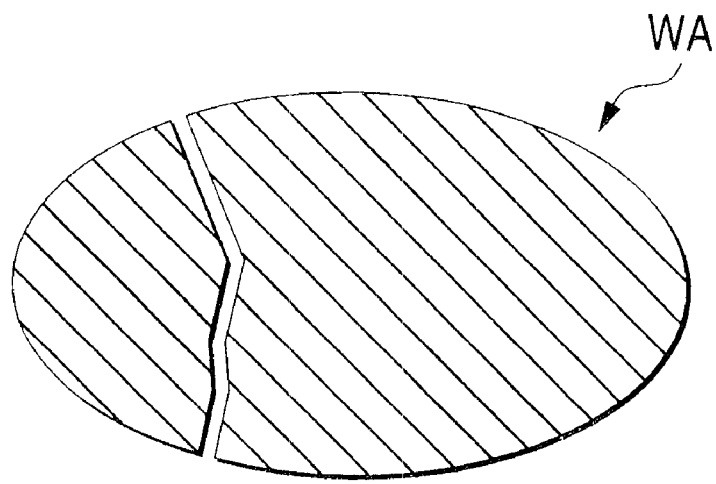
FIG. 4A is a diagram illustrating an X-ray perspective image of an object to be inspected WA in which cracks occur.
Figure 4B:
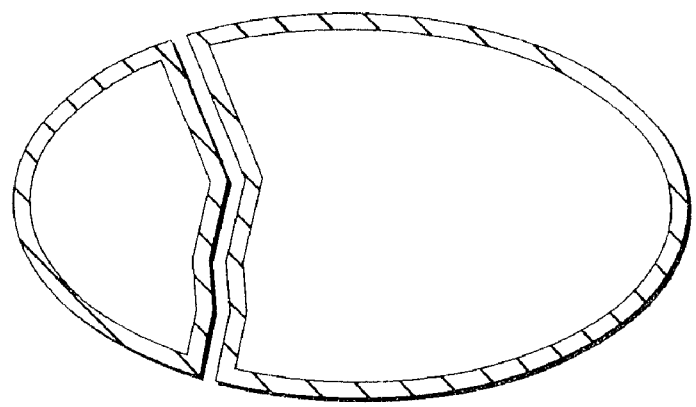
FIG. 4B is a diagram illustrating an image represented by the data, which is obtained by performing the difference processing on each of pixels in the case as shown in FIG. 4A.

That is, in the case that no crack and no nick occur in the object to be inspected WA, an image is constituted by the difference between the pixel data of pixels consisting the X-ray perspective image of the object WA so that only the contour portion of the object to be inspected WA is dark, as illustrated in FIG. 2D. The total number M of difference values included in the set gray level range of gray level profile from XL to XH is proportional to a circumference length of the object to be inspected WA. The value of this number M when no cracks or nicks occur is, for example, about 100, and thus the value of the number M is a larger value than 100, as described hereinbelow in the case that a crack or a nick occurs in the object to be inspected WA. Supposing now that the object to be inspected WA is cracked in the package as an X-ray perspective image illustrated in FIG. 4A, an image constituted by difference values obtained by difference processing is constructed, as illustrated in FIG. 4B. In this case, the total number M of difference values included in the set gray level range of gray level profile from XL to XH increases from the circumference length of the object to be inspected WA, in which no cracks occur, by the length of an additional contour portion due to the crack. Thus, the total number M is, for instance, about 160. Consequently, it can correctly be determined by setting the acceptance range between the values ML to MH to be a range from 90 to 110 whether or not a crack or a nick occurs in the object.

Incidentally, in the case that the gray level obtained from the difference value in an edge part of the package in an X-ray perspective image is included in the gray level range of gray level profile from XL to XH, the approximate number of the difference values in such a part is preliminarily estimated. Thus, it is sufficient that a number obtained by subtracting such an estimated number from the total number M is compared with the values between ML and MH of the acceptance range. Alternatively, it is sufficient that the acceptance range of the levels ML to MH is set by taking such an estimated number into consideration.

When the number M is within the acceptance range of the values from ML to MH, an acceptance decision treatment is performed. Conversely, when the number M is not within the acceptance range of the values from ML to MH, an abnormality decision treatment, such sounding of an alarm buzzer or exclusion of a commodity, is performed. Thereafter, the inspection apparatus proceeds to determination on whether or not a crack or a nick occurs in the next object to be inspected W.

The particularly noteworthy aspect of the aforementioned embodiment resides in that the presence/absence of a crack or a nick in the object to be inspected WA is determined by performing the difference processing on the pixel data, and then totalizing the number of pixels having gray level data included in the preset gray level range among the gray level data obtained by the difference processing, and deciding whether or not a result of the totalization is within the acceptance range, instead of determining the presence/absence of a crack or a nick in the object to be inspected WA by performing image processing, which uses pixel data outputted from the one-dimensional X-ray detector 3, to thereby recognize a pattern of the object to be inspected WA. As compared with the case of software for the determination based on the pattern recognition, the software for the determination according to the invention, which employs such data processing, is extremely simple. Thus, the inspection apparatus of the invention can use relatively simple hardware for performing such software.

As described above, according to the invention, radiation is irradiated onto object to be inspected. Thus, a perspective image of the object is obtained. Moreover, the difference between pixel data of each pixel consisting the perspective image and pixel data of each of surrounding pixels thereof is calculated. After the calculation of the difference, a total number of pixels, whose gray level data after difference processing are within a predetermined gray level range, is calculated. A value corresponding to a total of circumference length of the object to be inspected contained in the package is obtained from a result of the calculation of a total number of such pixels. Whether a crack or a nick occurs in the objects is determined according to whether or not the obtained value corresponding to a total of circumference length of the object to be inspected is within a predetermined range. Thus, the inspection apparatus of the invention can be used for inspection of object contained in a packaging container formed from a non-transmissive material, such as aluminum foil. Moreover, in the case of the inspection apparatus of the invention, data processing is easy to perform, as compared with the case that the inspection of the object is performed by recognizing a pattern of a radiation perspective image, similarly as a conventional foreign-object inspecting apparatus using radiation. Consequently, both the software and the hardware can be implemented at low cost. With low-cost configuration, the inspection apparatus of the invention can reliably determine whether or not a crack or a nick occurs in the object wrapped by a non-transmissive material.

What is claimed is:

1. A radiation inspection apparatus comprising:

a radiation generator for generating radiation toward an object to be inspected;

a radiation detector disposed in such a way to face said radiation generator, for detecting the radiation transmitted through the object to be inspected and outputting a pixel data of each pixel consisting an image of the object to be inspected; and a data processor unit for performing data processing by using the pixel data outputted from said radiation detector, wherein said data processor unit calculates a difference between that pixel data of each pixel, which is outputted from said radiation detector, and the pixel data of each of surrounding pixels thereof, and obtains a total of a circumference length of the object to be inspected by totalizing the number of pixels, gray level data obtained by difference processing correspondingly to each of which is within a predetermined gray level range, and determines from a total of the circumference length of the object whether or not a crack or a nick occurs in the object.

2. The radiation inspection apparatus according to claim 1, further comprising:

a conveying unit for conveying the object to be inspected between said radiation generator and said radiation detector.

3. The radiation inspection apparatus according to claim 1, wherein said data processor unit determines that a crack or a nick occurs in the object when the total of the circumference length of the object is out of an acceptance range.

4. A radiation inspection method comprising:

generating radiation toward an object to be inspected;

detecting the radiation transmitted through the object to be inspected to obtain a pixel data of each pixel consisting an image of the object to be inspected based on the detected radiation;

calculating a difference between the pixel data of each pixel, and the pixel data of each of surrounding pixels thereof;

obtaining a total of a circumference length of the object to be inspected by totalizing the number of pixels, gray level data obtained by difference processing correspondingly to each of which is within a predetermined gray level range; and determining from a total of the circumference length of the object whether or not a crack or a nick occurs in the object.

5. The radiation inspection method according to claim 4, wherein it is determined that a crack or a nick occurs in the object when the total of the circumference length of the object is out of an acceptance range.

* * * * *